(12) United States Patent
Uebayashi et al.

(10) Patent No.: US 8,724,879 B2
(45) Date of Patent: May 13, 2014

(54) MEDICAL IMAGE PROCESSING APPARATUS, A MEDICAL IMAGING APPARATUS, AND A METHOD OF PROCESSING MEDICAL IMAGES

(75) Inventors: Yoshinori Uebayashi, Nasushiobara (JP); Satoru Nakanishi, Utsunomiya (JP); Yasuhiro Noshi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 145 days.

(21) Appl. No.: 13/520,052

(22) PCT Filed: Oct. 25, 2011

(86) PCT No.: PCT/JP2011/074532
§ 371 (c)(1),
(2), (4) Date: Jun. 29, 2012

(87) PCT Pub. No.: WO2012/057126
PCT Pub. Date: May 3, 2012

(65) Prior Publication Data
US 2012/0288178 A1 Nov. 15, 2012

(30) Foreign Application Priority Data
Oct. 25, 2010 (JP) ................................ 2010-238133

(51) Int. Cl.
*G06K 9/00* (2006.01)
(52) U.S. Cl.
USPC ........... 382/131; 382/128; 382/130; 382/282; 128/922; 128/923
(58) Field of Classification Search
USPC .......... 382/128, 130, 131, 132, 282; 128/922, 128/923
See application file for complete search history.

(56) References Cited

U.S. PATENT DOCUMENTS 4,751,587 A 6/1988 Asahina
7,289,844 B2 * 10/2007 Misczynski et al. .......... 600/515
(Continued)

FOREIGN PATENT DOCUMENTS

JP 61 283967 12/1986
JP 08 308827 11/1996
(Continued)

OTHER PUBLICATIONS

International Search Report issued on Jan. 24, 2012 in PCT/JP11/074532 filed on Oct. 25, 2011.

*Primary Examiner* — Yosef Kassa
(74) *Attorney, Agent, or Firm* — Oblon, Spivak, McClelland, Maier & Neustadt, L.L.P.

(57) ABSTRACT

A medical image processing apparatus includes a difference calculator, a removal part, a first statistical processing part, and an estimation part. The difference calculator receives a plurality of medical image data with different imaging positions and obtains the difference between the plurality of medical image data, thereby generating difference image data that represents the difference. The removal part removes the region corresponding to a structure from the difference image data. The first statistical processing part obtains the first standard deviation of pixel values of each pixel of the difference image data with the region corresponding to the structure removed. The estimation part estimates the second standard deviation of the medical image data based on the first standard deviation. The medical image processing apparatus can estimate noise level of medical image data.

12 Claims, 12 Drawing Sheets

(56) References Cited

U.S. PATENT DOCUMENTS

| | | | |
|---|---|---|---|
| 7,318,000 B2 * | 1/2008 | Parvin et al. | 702/84 |
| 7,583,857 B2 * | 9/2009 | Xu et al. | 382/294 |
| 8,099,257 B2 * | 1/2012 | Parvin et al. | 702/179 |
| 8,121,382 B2 * | 2/2012 | Bohm et al. | 382/132 |
| 2005/0008115 A1 | 1/2005 | Tsukagoshi | |
| 2005/0053187 A1 | 3/2005 | Hagiwara | |

FOREIGN PATENT DOCUMENTS

| | | |
|---|---|---|
| JP | 2004 000530 | 1/2004 |
| JP | 2004 329661 | 11/2004 |
| JP | 2005 80918 | 3/2005 |
| JP | 2007 175194 | 7/2007 |

* cited by examiner

MEDICAL IMAGE PROCESSING APPARATUS, A MEDICAL IMAGING APPARATUS, AND A METHOD OF PROCESSING MEDICAL IMAGES

CROSS-REFERENCE TO RELATED APPLICATIONS

This application is based upon and claims the benefit of priority from Japanese Patent Applications No. 2010-238133, filed Oct. 25, 2010; the entire contents of all of which are incorporated herein by reference.

FIELD

Embodiments relate to a medical image processing apparatus, medical imaging apparatus, and method of processing medical images.

BACKGROUND

In order to improve the image quality of medical image data generated by medical imaging apparatuses such as an X-ray CT apparatus and an MRI apparatus, the noise level of the medical image data may be determined. For example, an operator sets a region of interest (ROI) in a region with a relatively small difference in the pixel values of each pixel in medical image data. A medical image processing apparatus, etc. targets image data within this region of interest to obtain the noise level. That is, the operator designates a set position in the region of interest.

However, if the operator sets the region of interest, the operation for this setting may be complicated. Moreover, in order to secure sufficient data to obtain the noise level, the operator has to set the region of interest in a region with a relatively small difference in pixel values of each pixel. However, in a region with many fine structures in a subject, the pixel values of each pixel vary. In this case, it is difficult for the operator to set the region of interest to secure data.

This embodiment is intended to provide a medical image processing apparatus, medical imaging apparatus, and method of processing medical images that can estimate the noise of medical image data.

DETAILED DESCRIPTION

The medical image processing apparatus according to this embodiment comprises a difference calculator, a removal part, a first statistical processor, and an estimation part. The difference calculator receives a plurality of medical image data with different imaging positions and determines the difference between the plurality of medical image data, so as to generate difference image data representing the difference. The removal part removes a region corresponding to a structure from the difference image data. The first statistical processor determines a first standard deviation of a pixel value for each pixel of the image data difference with the region corresponding to the structure removed. The estimation part estimates a second standard deviation of the medical image data of the pixel value of each pixel of medical image data based on the first standard deviation.

First Embodiment

Figure 1:
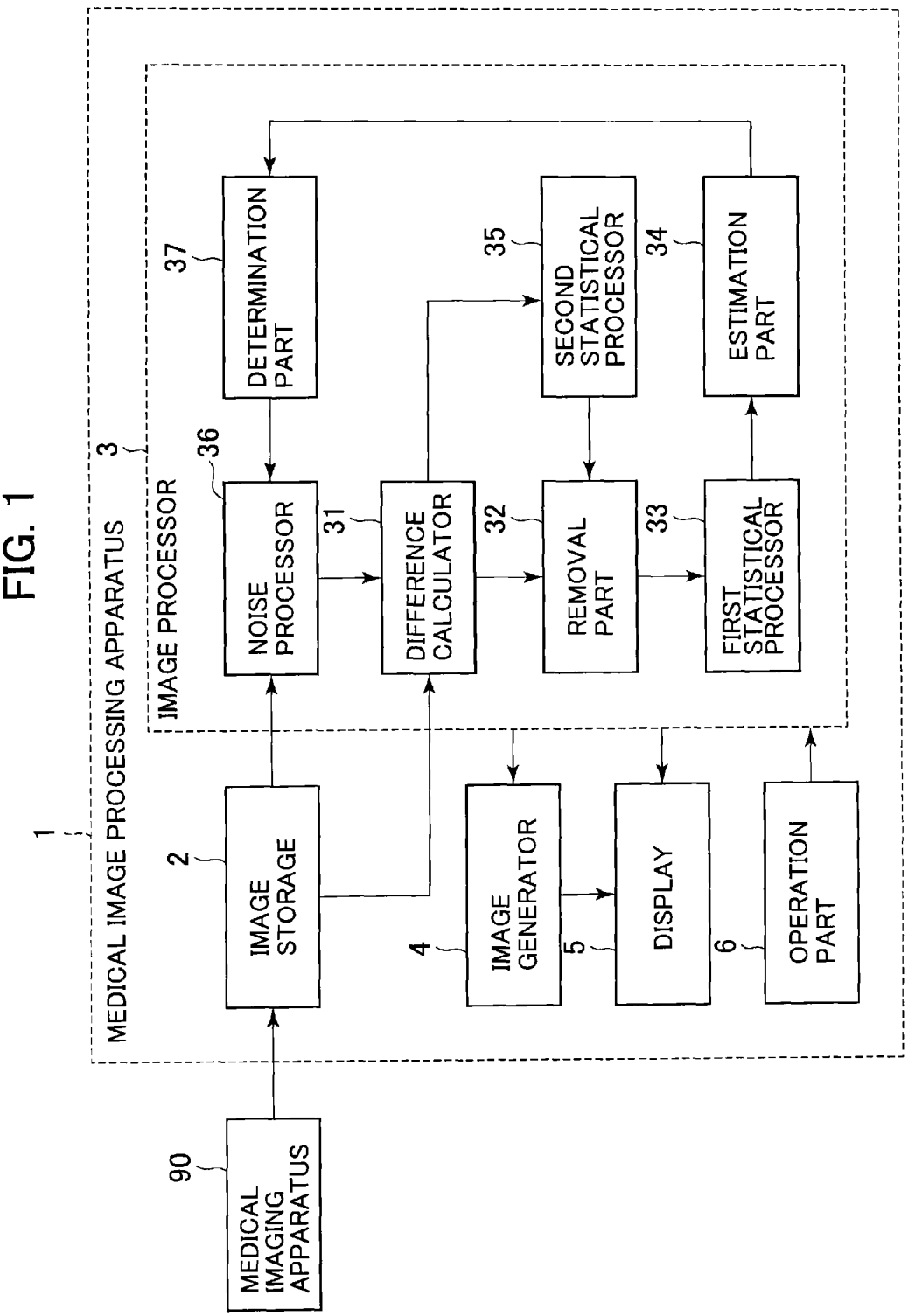
FIG. 1 is a block diagram of a medical image processing apparatus according to the first embodiment.

A medical image processing apparatus according to the first embodiment is described in reference to FIG. 1. FIG. 1 is a block diagram of the medical image processing apparatus according to the first embodiment. The medical image processing apparatus 1 according to the first embodiment is, for example, connected to a medical imaging apparatus 90.

(Medical Imaging Apparatus 90)

The medical imaging apparatus 90 may be an imaging apparatus, for example, an X-ray CT apparatus, an MRI apparatus, or an ultrasound imaging apparatus. The medical imaging apparatus 90 generates medical image data by imaging a subject. For example, the medical imaging apparatus 90 generates a plurality of medical image data imaged at different positions by imaging the subject at a plurality of different positions. In this way, the medical imaging apparatus 90 images a three-dimensional region of the subject. The medical imaging apparatus 90 corresponds to an example of the "imaging part."

In this embodiment, a case using an X-ray CT apparatus as the medical imaging apparatus 90 is described by way of example. The X-ray CT apparatus has an X-ray tube and an X-ray detector disposed on opposite sides of the subject. The X-ray CT apparatus radiates X-rays from the X-ray tube while rotating the X-ray tube and the X-ray detector around the subject. Moreover, the X-ray CT apparatus detects X-rays transmitted through the subject with the X-ray detector. Data detected by the X-ray detector is acquired by a data acquisition system (DAS) as projection data. Moreover, the X-ray CT apparatus reconfigures medical image data of the subject based on the acquired projection data. In the description below, the collection of detected data detected by the X-ray detector at an angle relative to the subject is referred to as a "view." For example, if the X-ray CT apparatus acquires projection data of one view per 1 degree in the rotational direction, it rotates the X-ray tube and the X-ray detector in one turn to acquire projection data of 360 views. The X-ray CT apparatus reconfigures the medical image data using the projection data of 360 views. In the description below, the direction of the body axis of the subject may be referred to as a "slice direction." Moreover, the position of the direction of the body axis may be referred to as a "slice position." Moreover, the rotational direction of the X-ray tube and the X-ray detector may be referred to as a "view direction." Moreover, for convenience of description, a three-dimensional orthogonal coordinate system defined with the X-axis, Y-axis, and Z-axis orthogonal to each other is defined. The direction of the body axis of the subject (slice direction) is defined as the Z-axis direction. The positions in respective cross-sections orthogonal in the direction of the body axis (Z-axis direction) at respective slice positions are defined by the X-axis and Y-axis.

For example, an X-ray CT apparatus acquires two-dimensional projection data from a plurality of views at each of a plurality of slice positions by imaging at the plurality of slice positions in the direction of the body axis of the subject (slice direction). The X-ray CT apparatus reconfigures the CT image data at each slice position based on the two-dimensional projection data of the plurality of views at each slice position. Volume data comprised of a plurality of CT image data is output from the medical imaging apparatus 90 to the medical image processing apparatus 1.

Moreover, the X-ray CT apparatus may image a three-dimensional imaging region having a width in the slice direction by using a two-dimensional X-ray detector (multi-array detector) comprising a plurality of detection elements in the slice direction. Moreover, the X-ray CT apparatus may acquire three-dimensional projection data of a width in the slice direction via this imaging. The X-ray CT apparatus can generate volume data based on the three-dimensional projection data of a plurality of views. Volume data comprised of the three-dimensional projection data of the plurality of views is output from the medical imaging apparatus 90 to the medical image processing apparatus 1.

In the description below, "projection data" may be two-dimensional projection data or three-dimensional projection data.

(Medical Image Processing Apparatus 1)

The medical image processing apparatus 1 according to the first embodiment comprises an image storage 2, an image processor 3, an image generator 4, a display 5, and an operation part 6.

(Image Storage 2)

The image storage 2 stores medical image data output from the medical imaging apparatus 90. For example, the image storage 2 stores volume data comprised of a plurality of CT image data. Moreover, the image storage 2 may store the projection data of a plurality of views output from the medical imaging apparatus 90.

(Image Processor 3)

The image processor 3 comprises a difference calculator 31, a removal part 32, a first statistical processor 33, an estimation part 34, a second statistical processor 35, a noise processor 36, and a determination part 37. The image processor 3 determines the Standard Deviation (SD). This standard deviation is the variation in pixel values of each pixel of medical image data. The case is described by way of example in which the image processor 3 determines the standard deviation SD of pixel values of each pixel of CT image data at the slice position (z1).

(Difference Calculator 31)

The difference calculator 31 retrieves a plurality of CT image data with mutually different slice positions imaged from the image storage 2. Moreover, the difference calculator 31 determines the difference between two sets of CT image data of which the slice positions are adjacent to each other. The difference calculator 31 generates first difference image data by determining the difference. The difference calculator 31 determines the difference in pixel values such as brightness for each pixel (x, y). The difference calculator 31 may generate one set of first difference image data. The difference calculator 31 may also generate a plurality of first difference image data. The difference calculator 31 outputs the first difference image data to the removal part 32 and the second statistical processor 35. The slice position (position in the Z-axis direction) may be designated by the operator using the operation part 6. For example, when the operator performs an operation of designating a desired region in the Z-axis direction using the operation part 6, coordinate information (coordinate information in the Z-axis direction) indicating the position of the desired region is output from the operation part 6 to the image processor 3. The difference calculator 31 retrieves a plurality of CT image data included in the desired region designated by the operation part 6 from the image storage 2. Moreover, the difference calculator 31 determines a difference between two sets of CT image data of which the slice positions are adjacent to each other. As an example, when the operator designates the slice position (z1) using the operation part 6, coordinate information of the slice position (z1) is output from the operation part 6 to the image processor 3. The difference calculator 31 retrieves the CT image data at the slice position (z1) and the CT image data at the slice position (z2) next to the slice position (z1) from the image storage 2. Subsequently, the difference calculator 31 generates first difference image data by determining the difference of the CT image data at the slice position (z1) and the CT image data at the slice position (z2).

(Removal Part 32)

The removal part 32 removes a region corresponding to a structure from the first difference image data by performing threshold processing on the first difference image data. For example, the removal part 32 leaves the region in which the pixel value is included in a predefined range in the first difference image data, and removes the region in which the pixel value is outside the predefined range. Namely, the removal part 32 determines the region in which the pixel value is larger than the upper threshold of the predefined range and the region in which the pixel value is smaller than the lower threshold of the predefined range to be a structure of the subject. Then, the removal part 32 removes the regions determined to be the structure of the subject from the first difference image data. For example, the removal part 32 may replace the pixel value of the region corresponding to the structure with a constant pixel value. Moreover, the removal part 32 may delete the region corresponding to the structure from the first difference image data. Moreover, the removal part 32 may replace the pixel value of the region corresponding to the structure with a surrounding pixel value. In the description below, the first difference image data with the region corresponding to the structure removed may be referred to as "second difference image data." The removal part 32 outputs the second difference image data from the first statistical processor 33.

Figure 2:
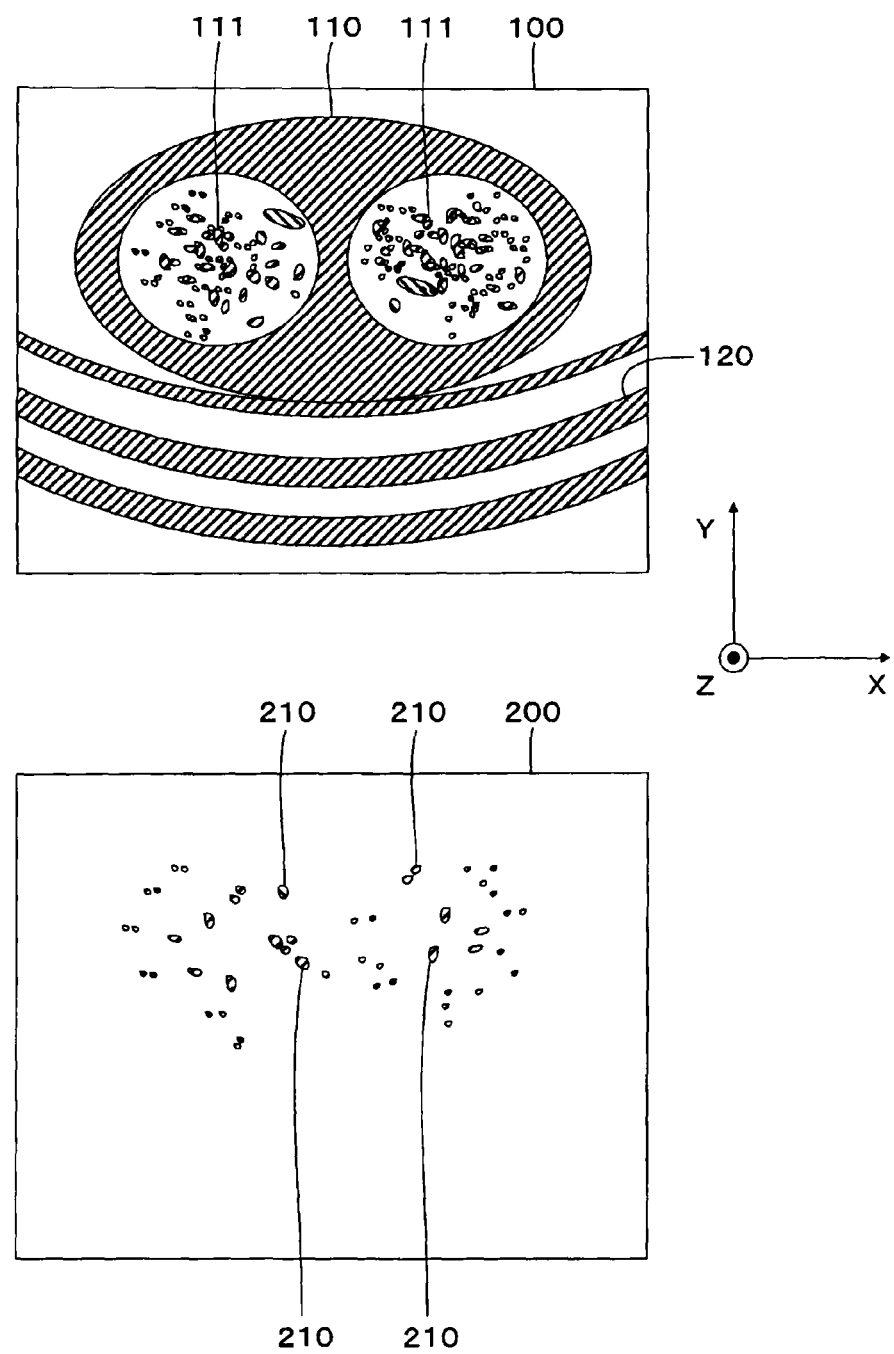
FIG. 2 is a diagram graphically showing a medical image and a difference image.

Processing of the removal part 32 is described in reference to FIG. 2. FIG. 2 is a diagram graphically showing a medical image and a difference image. FIG. 2 shows a CT image 100 and a difference image 200. The difference image 200 is an example of a first difference image. The CT image 100 is an image at a slice position (z1) in the direction of the body axis (slice direction). The CT image 100 represents an image of a subject image 110 and an image of a bed 120, etc. The CT image 100 represents a region 111 in which the distribution of pixel values is not uniform and the pixel values of each pixel vary. The difference image 200 is an image representing the difference between the CT image 100 at the slice position (z1) and the CT image 100 at the slice position (z2) next to the slice position (z1). The difference image 200 represents an image 210 corresponding to the structure. The removal part 32 removes an image 210 in which the pixel value is outside a predefined range in the difference image 200. For example, the removal part 32 may replace the pixel value of the image 210 with a constant pixel value. Moreover, the removal part 32 may delete the image 210 from the difference image 200. Moreover, the removal part 32 may replace the pixel value of the image 210 with a surrounding pixel value. The removal part 32 outputs the second difference image data with the image 210 corresponding to the structure removed to the first statistical processor 33.

(First Statistical Processor 33)

The first statistical processor 33 determines the standard deviation SD, which is the variation in pixel values of respective pixels of the second difference image data with the region corresponding to the structure removed. Hereinafter, the standard deviation SD of the second difference image data may be referred to as the "first standard deviation SD." The first statistical processor 33 outputs the first standard deviation SD to the estimation part 34.

(Estimation Part 34)

Figure 3:
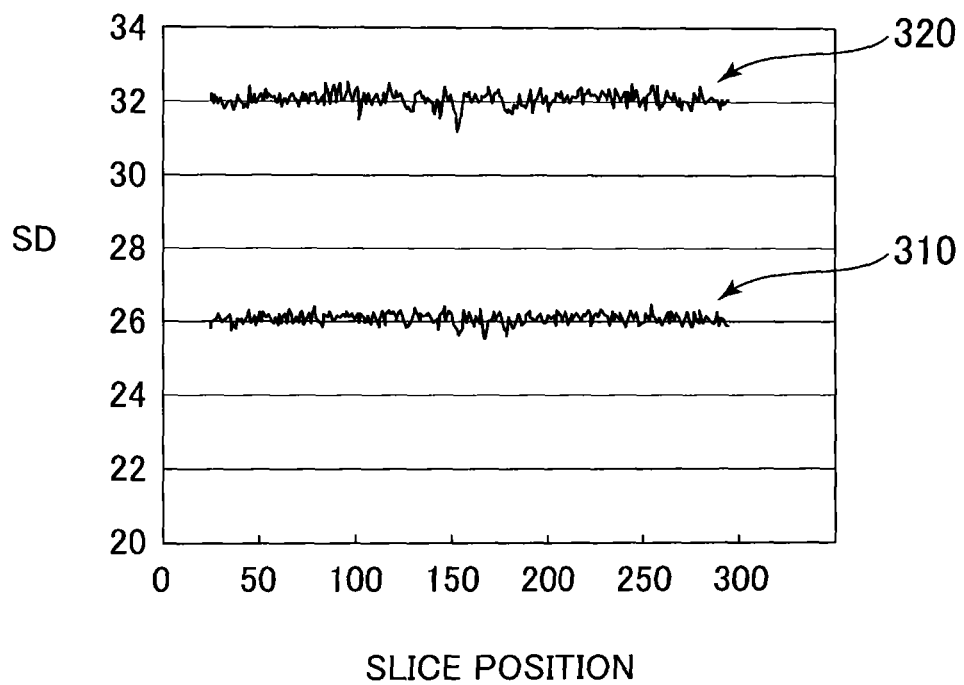
FIG. 3 is a graph showing the standard deviation SD of the medical image and the standard deviation SD of the difference image.

The estimation part 34 estimates the standard deviation SD, which is the variation in pixel values of each pixel of the CT image data, based on the first standard deviation SD. In the description below, the standard deviation SD of the CT image data may be referred to as the "second standard deviation SD." The estimation part 34 estimates the second standard deviation SD from the first standard deviation SD using a noise model representing the relationship between the first standard deviation SD of the second difference image data and the second standard deviation SD of the CT image data. The noise model is described in reference to FIG. 3. FIG. 3 is a graph showing the standard deviation of the medical image and the standard deviation of the difference image. In FIG. 3, the horizontal axis indicates the slice position and the vertical axis indicates the standard deviation SD. A graph 310 indicates the second standard deviation SD of the CT image data. The second standard deviation SD shown by the graph 310 is a value obtained by simulation. For the simulation, imaging conditions according to the X-ray CT apparatus and reconfiguration conditions of the CT image data are used as parameters. The imaging conditions and reconfiguration conditions include, for example, the X-ray tube voltage and X-ray tube current supplied to the X-ray tube, the slice thickness, the slice position, the number of arrays of a plurality of X-ray detectors arrayed in the direction of the body axis (slice direction), etc. A graph 320 indicates the first standard deviation SD of the second difference image data. The second standard deviation SD of the CT image data and the first standard deviation SD of the second difference image data change depending on the slice position. Based on the graph 310 and the graph 320, the ratio between the second standard deviation SD of the CT image data and the first standard deviation SD of the second difference image data can be determined per slice position.

The following equation (1) indicates the relationship between the second standard deviation SD of the CT image data and the first standard deviation SD of the second difference image data.

$$SD_{ORG}(z) = \text{Ratio}(z) \times SD_{dz}(z) \quad \text{Equation (1):}$$

$SD_{ORG}(z)$ is the second standard deviation SD of the CT image data.

$SD_{dz}(z)$ is the first standard deviation SD of the second difference image data.

Ratio (z) is the ratio of the standard deviation SD obtained per slice position based on the graph 310 and the graph 320. The ratio of the standard deviation SD, Ratio (z), is obtained in advance, and stored in a storage (not shown) in advance. In addition, the ratio of the standard deviation SD, Ratio (z), corresponds to an example of an "estimation coefficient."

The estimation part 34 determines the second standard deviation SD of the CT image data according to the first standard deviation SD and Equation (1). As an example, the estimation part 34 determines the second standard deviation SD of the CT image data at the position (z1) according to Equation (1).

The estimation part 34 may output the second standard deviation SD of the CT image data to the display 5. In this case, the display 5 displays the second standard deviation SD of the CT image data determined by the estimation part 34.

(Second Statistical Processor 35)

The second statistical processor 35 generates an SD map of the first difference image data by a so-called difference mapping method. For example, the second statistical processor 35 determines the standard deviation (SD) of pixel values of each pixel in a predefined region of the first difference image data. This standard deviation SD is referred to as the "third standard deviation." The second statistical processor 35 moves this predefined region across the first difference image data to obtain the standard deviation SD (third standard deviation) at each position. The second statistical processor 35 generates the SD map representing the distribution of the third standard deviation based on the results determined. As an example, the second statistical processor 35 determines the standard deviation SD (third standard deviation) of pixel values within a (11×11) pixel region in the first difference image data. Moreover, the second statistical processor 35 moves the (11×11) pixel region across the first difference image data to determine the standard deviation SD (third standard deviation) at each position. The second statistical processor 35 generates a SD map representing the distribution of the third standard deviation based on the results obtained. The second statistical processor 35 outputs the SD map of the first difference image data to the removal part 32.

The removal part 32 removes a region corresponding to a structure from the SD map by performing threshold processing on the SD map of the first difference image data. For example, the removal part 32 leaves the region in which the third standard deviation is included in a predefined range in the SD map of the first difference image data, and removes the region in which the third standard deviation is outside the predefined range. That is, the removal part 32 determines the region in which the third standard deviation is larger than the upper threshold of the predefined range and the region in which the third standard deviation is smaller than the lower threshold of the predefined range to be a structure of the subject. Subsequently, the removal part 32 removes the regions determined to be the structure of the subject from the SD map of the first difference image data.

Figure 4:
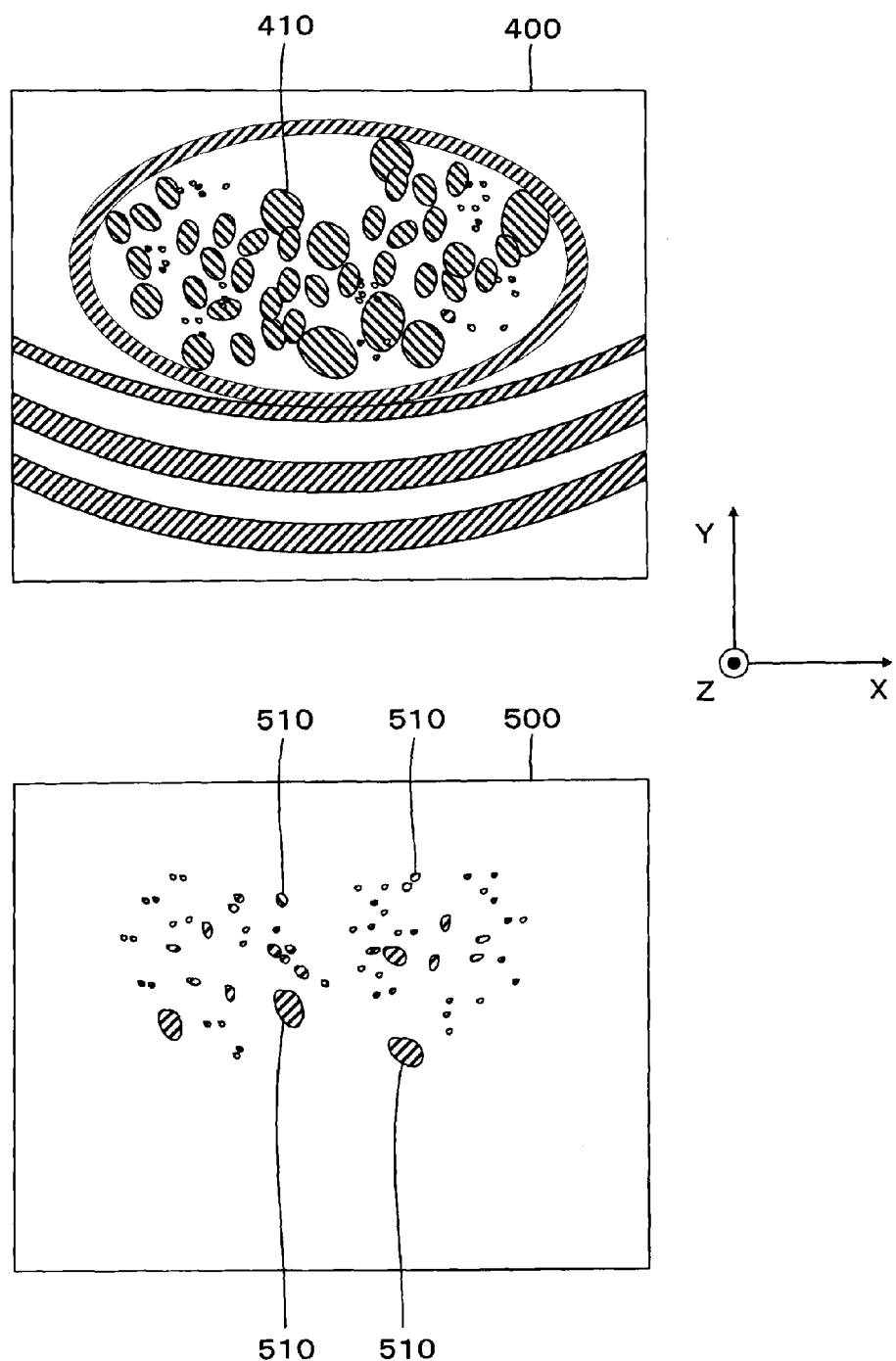
FIG. 4 is a diagram graphically showing a SD map of the medical image and a SD map of the difference image.

A SD map is described in reference to FIG. 4. FIG. 4 is a diagram graphically showing a SD map of the medical image and a SD map of the difference image. FIG. 4 shows a SD map 400 of the CT image data and a SD map 500 of the first difference image data. The SD map 400 is a SD map of the CT image data at a specific slice position (z1). The SD map 400 represents an image 410, etc. resulting from a subject. In this way, the SD map 400 of the CT image data represents the image 410 in which distribution of the standard deviation SD is not uniform and the standard deviation SD varies. The SD map 500 of the first difference image data is a SD map of the difference between the CT image at the slice position (z1) and the CT image at the slice position (z2) next to the slice position (z1). The SD map 500 represents an image 510 corresponding to the structure. The removal part 32 removes the image 510 in which the standard deviation SD is outside a predefined range in the SD map 500. For example, the removal part 32 may replace a value of the image 510 with a constant value. Moreover, the removal part 32 may delete the image 510 from the SD map 500. Moreover, the removal part 32 may replace the pixel value of the image 510 with a surrounding value. The removal part 32 outputs the SD map with the image 510 corresponding to the structure removed to the first statistical processor 33.

Figure 5:
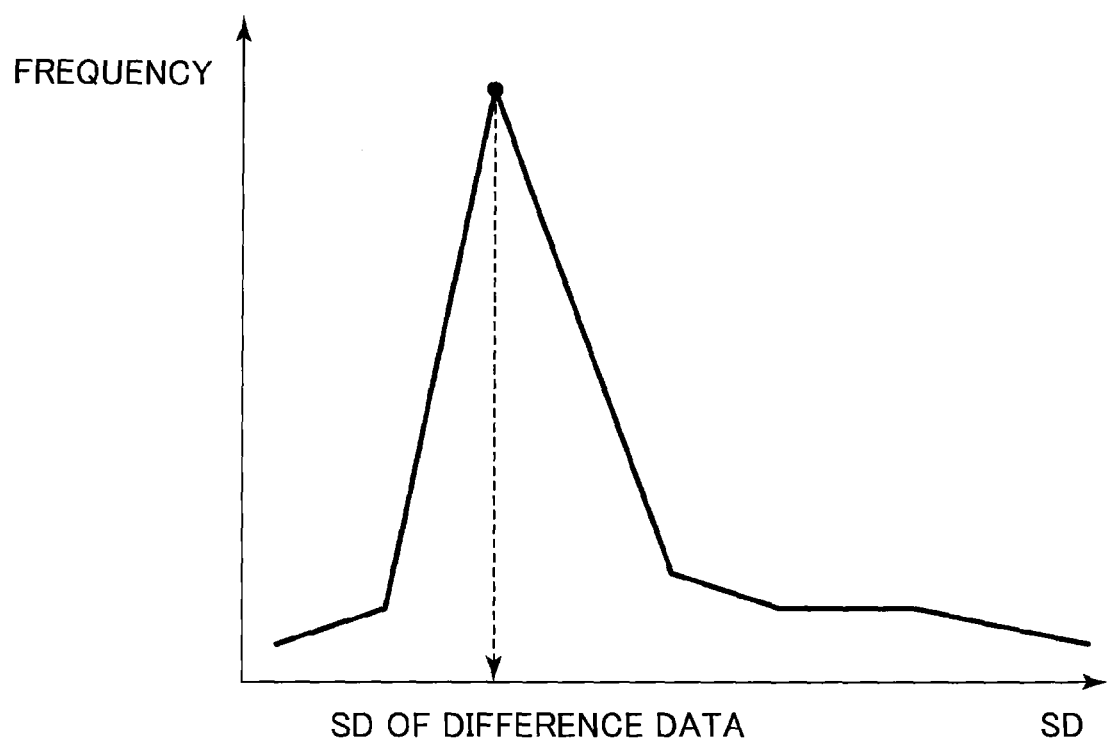
FIG. 5 is a diagram graphically showing a histogram created from the SD map of the difference image.

The first statistical processor 33 determines the first standard deviation SD of the difference image data based on the SD map with the region corresponding to the structure removed. For example, the first statistical processor 33 creates a histogram that represents the frequency of the standard deviation in the SD map. Moreover, the first statistical processor 33 determines the first standard deviation SD of the difference image data based on this histogram. The histogram is shown in FIG. 5. In FIG. 5, the horizontal axis is the standard deviation SD in the SD map, while the vertical axis is the frequency of the standard deviation SD. The first statistical processor 33 determines a statistical value from the histogram. Moreover, the first statistical processor 33 defines the statistical value as the first standard deviation SD of the difference image data. For example, the first statistical processor 33 determines a mode value of the histogram, as shown in FIG. 5. Moreover, the first statistical processor 33 defines the mode value as the first standard deviation SD. Alternatively, the first statistical processor 33 determines a median value, a centroid value, or an average value of the histogram. Moreover, the first statistical processor 33 may define any of these to be the first standard deviation SD. The first statistical processor 33 outputs the first standard deviation SD to the estimation part 34. Moreover, the first statistical processor 33 may limit the effective range of the histogram to determine a statistical value. For example, the first statistical processor 33 may exclude 5% of the upper and lower limits of the histogram to determine a statistical value.

The estimation part 34 determines the second standard deviation SD of the CT image data at the slice position (z1) according to the aforementioned equation (1).

(Noise Processor 36)

The noise processor 36 retrieves a plurality of CT image data from the image storage 2. Moreover, the noise processor 36 performs noise-reduction processing on the plurality of CT image data. For example, the noise processor 36 performs noise-reduction processing on the CT image data using a low-pass filter (LPF). The noise processor 36 outputs the CT image data treated with noise-reduction processing to the difference calculator 31.

The difference calculator 31, the removal part 32, the first statistical processor 33, the estimation part 34, and the second statistical processor 35 execute the aforementioned processing on the CT image data treated by noise-reduction processing. With this processing, the estimation part 34 determines the second standard deviation SD of the CT image data treated by noise-reduction processing. Moreover, the estimation part 34 outputs the second standard deviation SD to the determination part 37.

(Determination Part 37)

The determination part 37 determines whether or not to perform noise-reduction processing based on the second standard deviation SD of the CT image data. For example, the determination part 37 determines to perform noise-reduction processing if the second standard deviation SD of the CT image data is above a preset threshold. Moreover, the determination part 37 determines not to perform noise-reduction processing if the second standard deviation SD is less than the threshold. The determination part 37 outputs information indicating the determination results to the noise processor 36.

If it is determined to perform noise-reduction processing, the noise processor 36 performs noise-reduction processing on the CT image data again. If it is determined not to perform noise-reduction processing, the noise processor 36 does not perform noise-reduction processing.

(Image Generator 4)

The image generator 4 generates three-dimensional image data that sterically represents the shape of the tissue by performing volume rendering on volume data. Moreover, the image generator 4 may generate image data (MPR image data) processing in any arbitrary cross-section by performing MPR (Multi Planar Reconstruction) on the volume data. Moreover, the image generator 4 may reconfigure medical image data such as three-dimensional image data based on the projection data of a plurality of views.

(Display 5 and Operation Part 6)

The display 5 is comprised of a monitor such as CRT and a liquid crystal display. The display 5 displays the standard deviation SD determined by the image processor 3. The display 5 may display three-dimensional images and MPR images generated by the image generator 4. The operation part 6 is comprised of input devices such as a keyboard and a mouse.

Respective functions of the image processor 3 and the image generator 4 may be executed by programs. As an example, the image processor 3 and the image generator 4 may be comprised of a processing unit (not shown) and a storage (not shown). As this processing unit, CPU, GPU, ASIC, etc., respectively, can be used. Moreover, as the storage, ROM, RAM, HDD, etc. can be used. An image processing program and an image generating programs are stored in the storage. The image processing program is used for execution of the function of the image processor 3. The image generating program is used for execution of the function of the image generator 4. The image generating program includes a difference calculating program, a removal program, a first statistical processing program, and an estimation program. The difference calculating program is used for execution of the function of the difference calculator 31. The removal program is used for execution of the function of the removal part 32. The first statistical processing program is used for execution of the function of the first statistical processor 33. The estimation program is used for execution of the function of the estimation part 34. Moreover, the image processing program may include a second statistical processing program that is used for execution of the function of the second statistical processor 35. Furthermore, the image processing program may include a noise processing program and a determination program. The noise processing program is used for execution of the function of the noise processor 36. The determination program is used for execution of the function of the determination part 37. The processing unit such as CPU executes the function of each part by executing the program stored in the storage. The process of image processing with the image processing program corresponds to an example of the "method of processing medical images."

(Operation)

Figure 6:
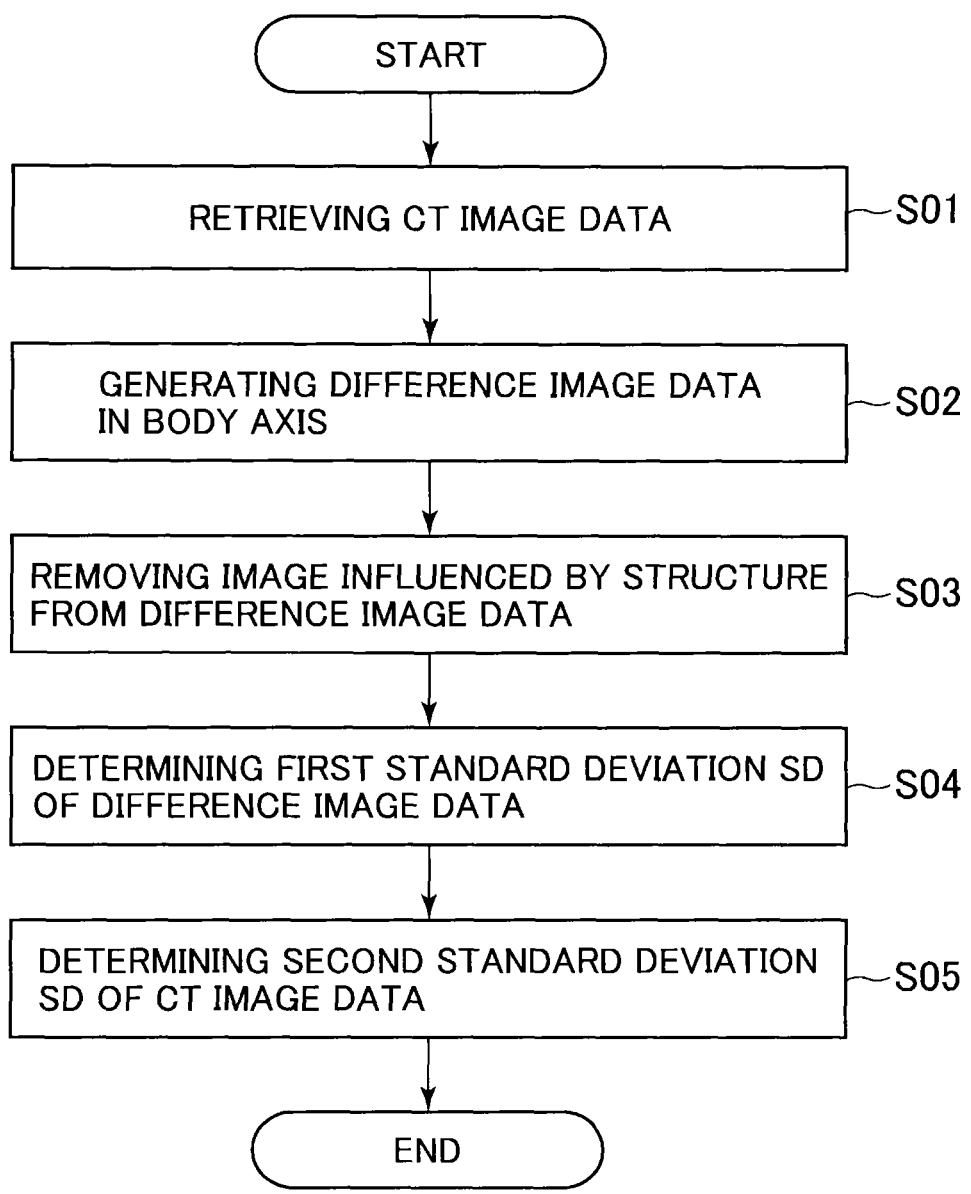
FIG. 6 is a flowchart showing the first operation with the medical image processing apparatus according to the first embodiment.
Figure 7:
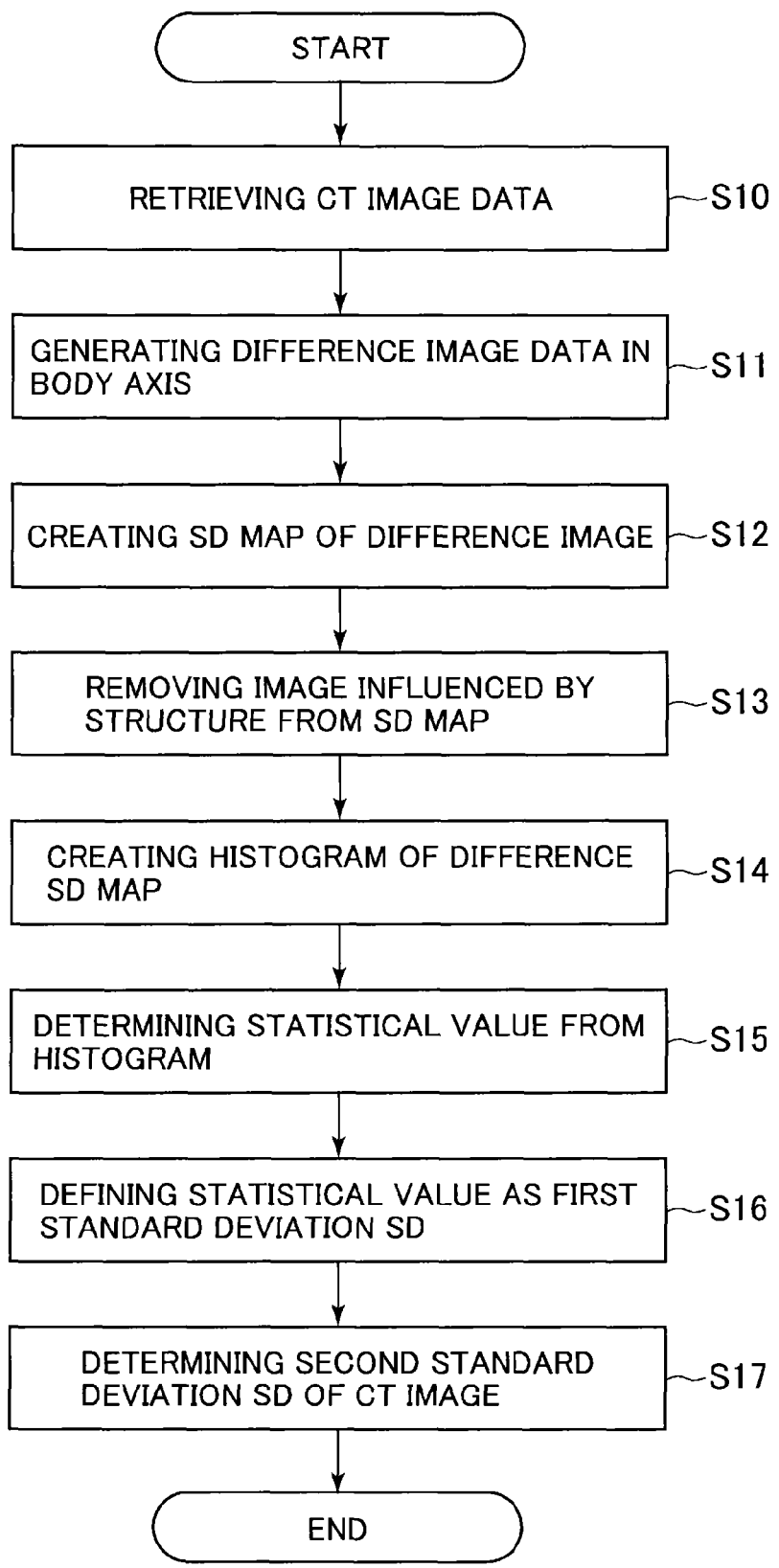
FIG. 7 is a flowchart showing the second operation with the medical image processing apparatus according to the first embodiment.
Figure 8:
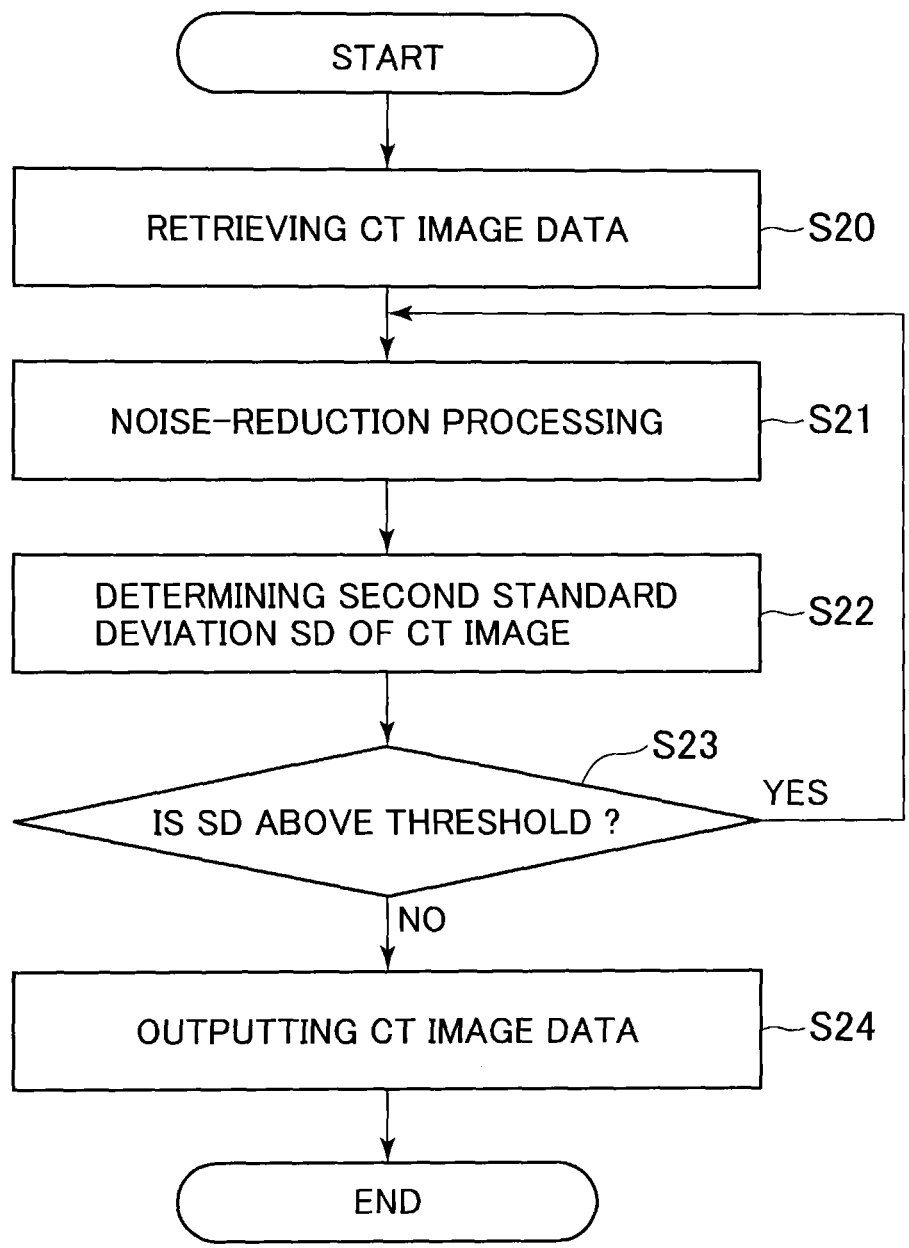
FIG. 8 is a flowchart showing the third operation with the medical image processing apparatus according to the first embodiment.

With reference to FIGS. 6 through 8, the operation with the medical image processing apparatus 1 according to the first embodiment is described. The medical image processing apparatus 1 executes any of a different first operation, second operation, and third operation, respectively.

(First Operation)

The first operation is described in reference to the flowchart in FIG. 6.

(Step S01)

First, the difference calculator 31 retrieves a plurality of CT image data captured at different slice positions from the image storage 2. For example, when the operator performs operations of designating the slice position (z1) using the operation part 6, coordinate information indicating the slice position (z1) is output from the operation part 6 to the difference calculator 31. The difference calculator 31 retrieves CT image data at the slice position (z1) and CT image data at the slice position (z2) next to the slice position (z1) from the image storage 2.

(Step S02)

The difference calculator 31 generates first difference image data by determining the difference between the plurality of CT image data with respective slice positions adjacent to each other. As an example, the difference calculator 31 generates the first difference image data by determining the difference between the CT image data of the slice position (z1) and the CT image data of the slice position (z2).

(Step S03)

The removal part 32 removes the region corresponding to a structure from the first difference image data by performing threshold processing on the first difference image data. The first difference image data with the region corresponding to the structure removed is referred to as "second difference image data."

(Step S04)

The first statistical processor 33 determines the first standard deviation SD, which is the variation in pixel values of each pixel of the second difference image data.

(Step S05)

The estimation part 34 determines the second standard deviation SD, which is the variation in pixel values of each pixel of the CT image data, based on the first standard deviation SD. Specifically, the estimation part 34 determines the second standard deviation SD of the CT image data at the slice position (z1) according to the equation (1) above.

The estimation part 34 outputs the second standard deviation SD of the CT image data to the display 5. The display 5 displays the second standard deviation SD of the CT image data.

As above, even though the CT image data has a region in which the distribution of pixel values is not uniform and the pixel values of each pixel vary, difference image data including fewer regions of uneven pixel values than the CT image data can be determined when the X-ray CT apparatus determines the difference between two CT image data adjacent to each other. In the difference image data, there are fewer regions in which the distribution of pixel values is not uniform. Therefore, it is possible to easily remove the region corresponding to the structure from the difference image data. Consequently, in the difference image data, distribution of pixel values becomes uniform over a wider region, making it possible to secure a sufficient number of data to obtain the noise level. Then, by estimating the second standard deviation SD of the CT image data from the first standard deviation SD of the difference image data using the noise model, it is possible to obtain the noise level of the CT image data even though the operator does not set a region of interest.

(Second Operation)

The second operation is described in reference to the flowchart in FIG. 7.

(Step S10)

First, the difference calculator 31 retrieves a plurality of CT image data captured at different slice positions from the image storage 2. For example, when the operator performs operations of designating the slice position (z1) using the operation part 6, coordinate information indicating the slice position (z1) is output from the operation part 6 to the difference calculator 31. The difference calculator 31 retrieves CT image data at the slice position (z1) and CT image data at the slice position (z2) next to the slice position (z1) from the image storage 2.

(Step S11)

The difference calculator 31 generates the first difference image data by determining the difference between the plurality of CT image data with respective slice positions adjacent to each other. As an example, the difference calculator 31 generates the first difference image data by determining the difference between the CT image data of the slice position (z1) and the CT image data of the slice position (z2).

(Step S12)

The second statistical processor 35 generates a SD map of the first difference image data by a so-called difference mapping method.

(Step S13)

The removal part 32 removes the region corresponding to a structure from the SD map by performing threshold processing on the SD map of the first difference image data.

(Step S14)

The first statistical processor 33 creates a histogram that represents the frequency of the standard deviation in the SD map with the region corresponding to the structure removed.

(Step S15)

The first statistical processor 33 determines a statistical value from the histogram of the SD map. For example, the first statistical processor 33 determines a mode value, a median value, a centroid value, or an average value as the statistical value.

(Step S16)

The first statistical processor 33 defines the statistical value as the first standard deviation SD of the difference image data. For example, the first statistical processor 33 defines any of the mode value, the median value, centroid value, and average value of the histogram as the first standard deviation SD of the difference image data.

(Step S17)

The estimation part 34 determines the second standard deviation SD of the CT image data at the slice position (z1) according to the aforementioned equation (1).

The estimation part 34 outputs the second standard deviation SD of the CT image data to the display 5. The display 5 displays the second standard deviation SD of the CT image data.

As above, even though the CT image data has a region in which the distribution of standard deviation SD is not uniform and the pixel values of each pixel vary, an SD map of the difference image data, with fewer regions of uneven standard deviation SD than an SD map of the CT image data, can be determined when the X-ray CT apparatus obtains the difference between two sets of CT image data adjacent to each other. In the SD map of the difference image data, there are fewer regions in which distribution of the standard deviation SD is not uniform. Therefore, it is possible to easily remove the region corresponding to the structure from the SD map of the difference image data. Consequently, in the SD map of the difference image data, distribution of the standard deviation SD becomes uniform over a wider region, making it possible to secure sufficient data to obtain the noise level. Subsequently, by using the noise model and estimating the second standard deviation SD of the CT image data from the first standard deviation SD of the difference image data, it is possible to obtain the noise level of the CT image data even though the operator does not set a region of interest.

(Third Operation)

The third operation is described in reference to the flowchart in FIG. 8.

(Step S20)

First, the noise processor 36 retrieves a plurality of CT image data captured at different slice positions from the image storage 2. For example, when the operator performs operations of designating a desired region in the Z-axis direction using the operation part 6, coordinate information (coordinate information in the Z-axis direction) indicating the position of the desired region is output from the operation part 6 to the image processor 3. The noise processor 36 retrieves a plurality of CT image data included in the desired region designated by the operation part 6 from the image storage 2.

(Step S21)

The noise processor 36 performs noise-reduction processing on the plurality of CT image data included in the desired region designated by the operation part 6 using a low-pass filter (LPF).

(Step S22)

The difference calculator 31, the removal part 32, the first statistical processor 33, and the estimation part 34 execute the aforementioned first operation on the CT image data treated with noise-reduction processing. Alternatively, the difference calculator 31, the removal part 32, the first statistical processor 33, the estimation part 34, and the second statistical processor 35 may also execute the aforementioned second operation on the CT image data treated with noise-reduction processing. With the first operation or the second operation executed, the estimation part 34 determines the second standard deviation SD of the CT image data treated with noise-reduction processing.

(Step S23)

The determination part 37 determines whether or not to perform noise-reduction processing based on the second standard deviation SD of the CT image data. For example, the determination part 37 determines to perform noise-reduction processing if the second standard deviation SD of the CT image data is above a preset threshold (Step S23, YES). Meanwhile, the determination part 37 determines not to perform noise-reduction processing if the second standard deviation SD is less than the threshold (Step S23, NO).

If it is determined to perform noise-reduction processing (Step S23, YES), the processing at Step S21 and Step S22 is repeatedly executed. That is, by performing noise-reduction processing on the plurality of CT image data included in the desired region again (Step S21), and executing the first operation or second operation on the CT image data treated with noise-reduction processing, the second standard deviation SD of the CT image data is determined. Subsequently, the processing at Step S21 and Step S22 is repeatedly executed until the second standard deviation SD of the CT image data becomes less than the threshold.

(Step S24)

If it is determined not to perform noise-reduction processing (Step S23, NO), the image processor 3 outputs the CT image data treated with noise-reduction processing (Step S24). For example, the image processor 3 outputs the plurality of CT image data treated with noise-reduction processing to the image generator 4. The image generator 4 may generate three-dimensional image data and MPR image data based on the plurality of CT image data.

As above, by determining whether or not to execute noise-reduction processing based on the second standard deviation SD of the CT image data, it is possible to automatically stop noise-reduction processing at the point when the second standard deviation SD reaches less than the threshold.

The medical image processing apparatus 1 according to the first embodiment may execute any of the first action, second action, and third action. For example, when the operator designates a desired operation among the first action, second action, and third action using the operation part 6, the medical image processing apparatus 1 may be allowed to execute the designated operation. If only the first operation is executed, the medical image processing apparatus 1 may not comprise the second statistical processor 35, the noise processor 36, and the determination part 37. Moreover, if only the second operation is executed, the medical image processing apparatus 1 may not comprise the noise processor 36 and the determination part 37.

In addition, the medical imaging apparatus 90 may comprise the function of a medical image processing apparatus 1A.

Second Embodiment

Figure 9:
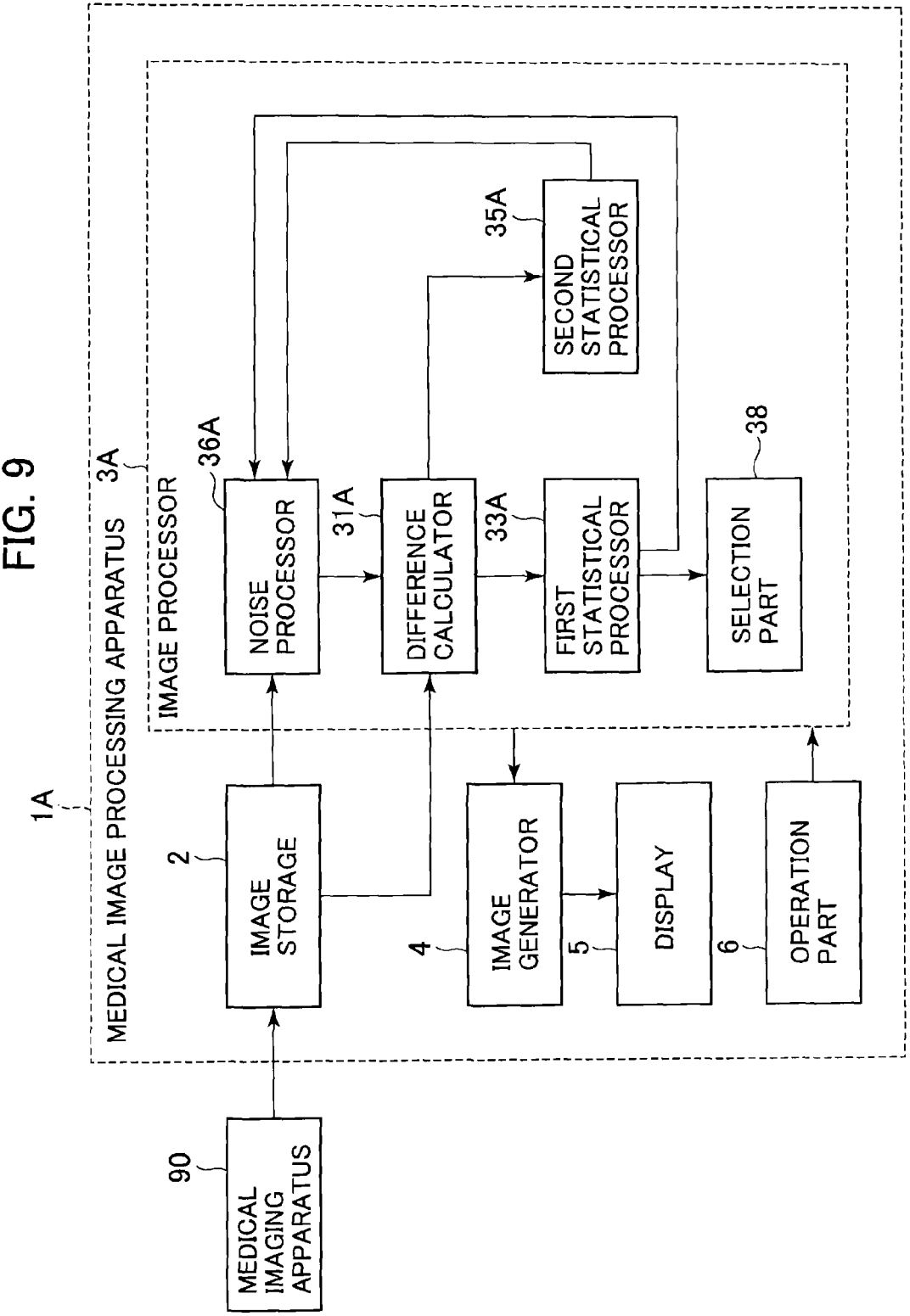
FIG. 9 is a block diagram of the medical image processing apparatus according to the second embodiment.

The medical image processing apparatus according to the second embodiment is described in reference to FIG. 9. FIG. 9 is a block diagram of the medical image processing apparatus according to the second embodiment. The medical image processing apparatus 1A according to the second embodiment is connected to the medical imaging apparatus 90 similarly to the first embodiment.

(Medical Image Processing Apparatus 1A)

The medical image processing apparatus 1A according to the second embodiment comprise an image storage 2, an image processor 3A, an image generator 4, a display 5, and an operation part 6.

(Image Processor 3A)

The image processor 3A comprises a difference calculator 31A, a first statistical processor 33A, a second statistical processor 35A, and a noise processor 36A.

(Image Storage 2)

The image storage 2 stores the projection data of a plurality of views acquired by the medical imaging apparatus 90. The image storage 2 may store two-dimensional projection data or three-dimensional projection data.

(Difference Calculator 31A)

The difference calculator 31A retrieves the projection data of a plurality of views with mutually different angles from the view direction from the image storage 2, and determines the difference between two sets of projection data with the angles from the view direction adjacent to each other, generating a plurality of difference projection data. For example, the difference calculator 31 determines the difference between two sets of projection data with the angles from the view direction adjacent to each other, targeting projection data of 1,200 views. In this way, the difference calculator 31A generates difference projection data for 1,200 views. The difference calculator 31A outputs the difference projection data to the first statistical processor 33A and the second statistical processor 35A.

(First Statistical Processor 33A)

The first statistical processor 33A determines the standard deviation SD, which is unevenness in pixel values of each pixel of the difference projection data. For the projection data of 1,200 views for example, the first statistical processor 33A determines the standard deviation SD for 1,200 views. The first statistical processor 33A may create a graph of the standard deviation SD of a plurality of views. The first statistical processor 33A outputs the standard deviation SD of the difference projection data to the noise processor 36A and a selection part 38.

Figure 10:
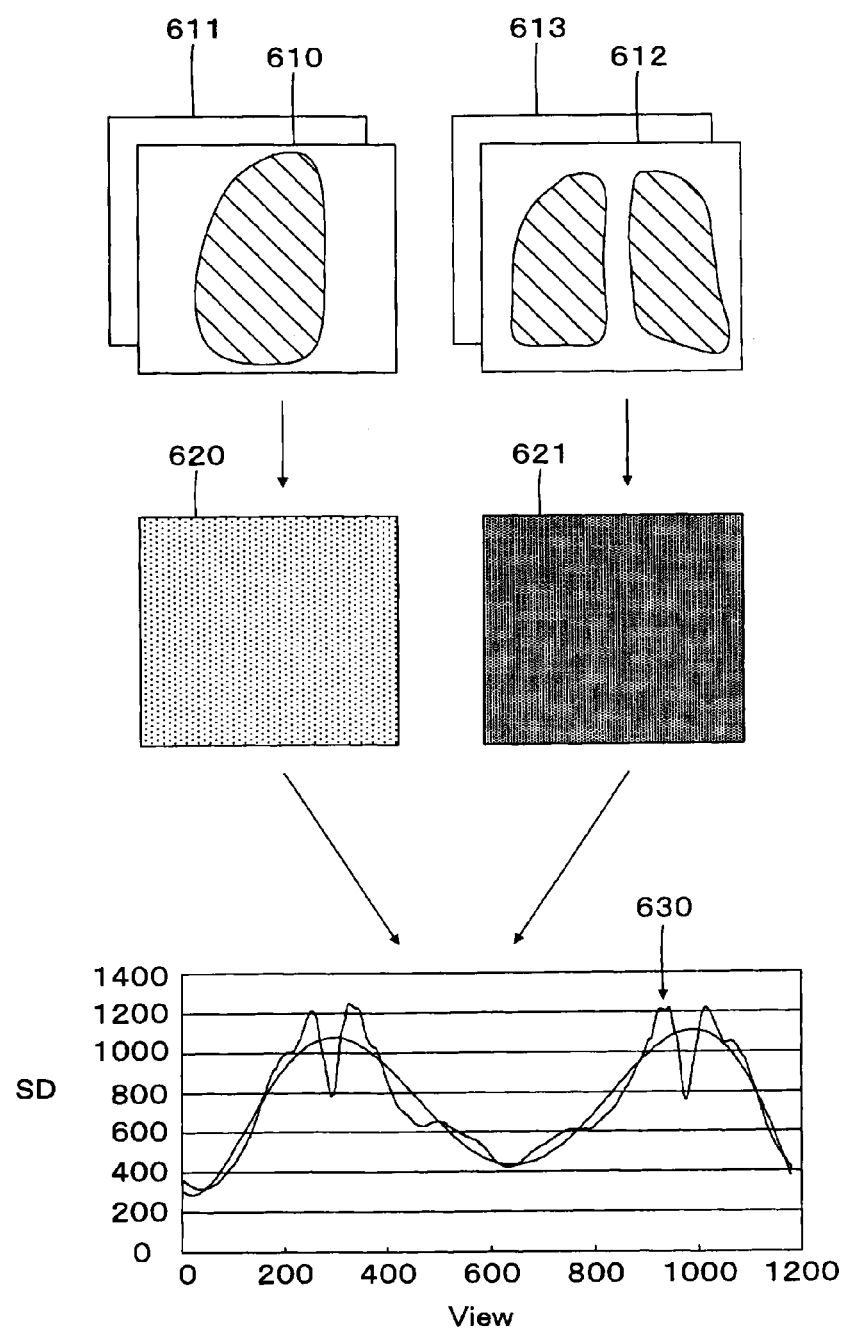
FIG. 10 is a diagram graphically showing projection data, difference projection data, and a standard deviation SD graph.

A specific example is described in reference to FIG. 10. FIG. 10 is a diagram graphically showing projection data, difference projection data, and a standard deviation SD graph. The difference calculator 31A generates difference projection data 620 by determining the difference between projection data 610 in a specific view ($\phi1$) and projection data 611 in a view ($\phi2$) next to the view ($\phi1$). Moreover, the difference calculator 31A generates difference projection data 621 by determining the difference between projection data 612 in another view ($\phi3$) and projection data 613 in a view ($\phi4$) next to the view ($\phi3$). The first statistical processor 33A determines the standard deviation SD of the difference projection data 620, 621. For the projection data of 1,200 views for example, the difference calculator 31A generates difference projection data for 1,200 views. Moreover, the first statistical processor 33A determines the standard deviation SD for 1,200 views. The graph 630 shown in FIG. 10 is a graph showing the standard deviation SD for 1,200 views.

(Noise Processor 36A)

The noise processor 36A performs noise-reduction processing on the projection data with the standard deviation SD of the difference projection data above a preset threshold. Similar to the first embodiment, the noise processor 36A may perform noise-reduction processing on the projection data using a low-pass filter LPF.

When processing with the noise processor 36A is completed, the image processor 3A outputs the projection data of a plurality of views to the image generator 4. That is, the image processor 3A outputs the projection data of the plurality of views including the projection data treated with noise-reduction processing to the image generator 4. The image generator 4 reconfigures medical image data such as three-dimensional image data based on the projection data of the plurality of views.

As above, the X-ray CT apparatus in the second embodiment performs noise-reduction processing on the projection data with the standard deviation SD of the difference projection data above the threshold. Therefore, it is possible to reduce noise while minimizing deterioration of data quality due to noise-reduction processing. When noise-reduction processing is performed on all projection data, the quality of all the data deteriorates. With regard to this, the X-ray CT apparatus in the second embodiment performs noise-reduction only on the projection data with the standard deviation SD of the difference projection data above the threshold and a relatively high noise level. In this way, the X-ray CT apparatus is enabled to reduce noise while minimizing deterioration of the data quality.

(Second Statistical Processor 35A)

The second statistical processor 35A generates a SD map of the difference projection data by a so-called difference mapping method. Similar to the first embodiment, the second statistical processor 35A determines the standard deviation SD of the pixel values of each pixel in a predefined region of the difference projection data. Moreover, the second statistical processor 35 displaces this predefined region across the difference projection data to determine the standard deviation SD at each position. The second statistical processor 35 generates a SD map representing the distribution of the standard deviation SD through this processing. The second statistical processor 35A outputs the SD map to the noise processor 36A.

The noise processor 36A specifies regions with the standard deviation SD above a preset threshold in the SD map of the difference projection data. Subsequently, the noise processor 36A performs noise-reduction processing on the projection data of regions with the standard deviation SD above the threshold.

Figure 11:
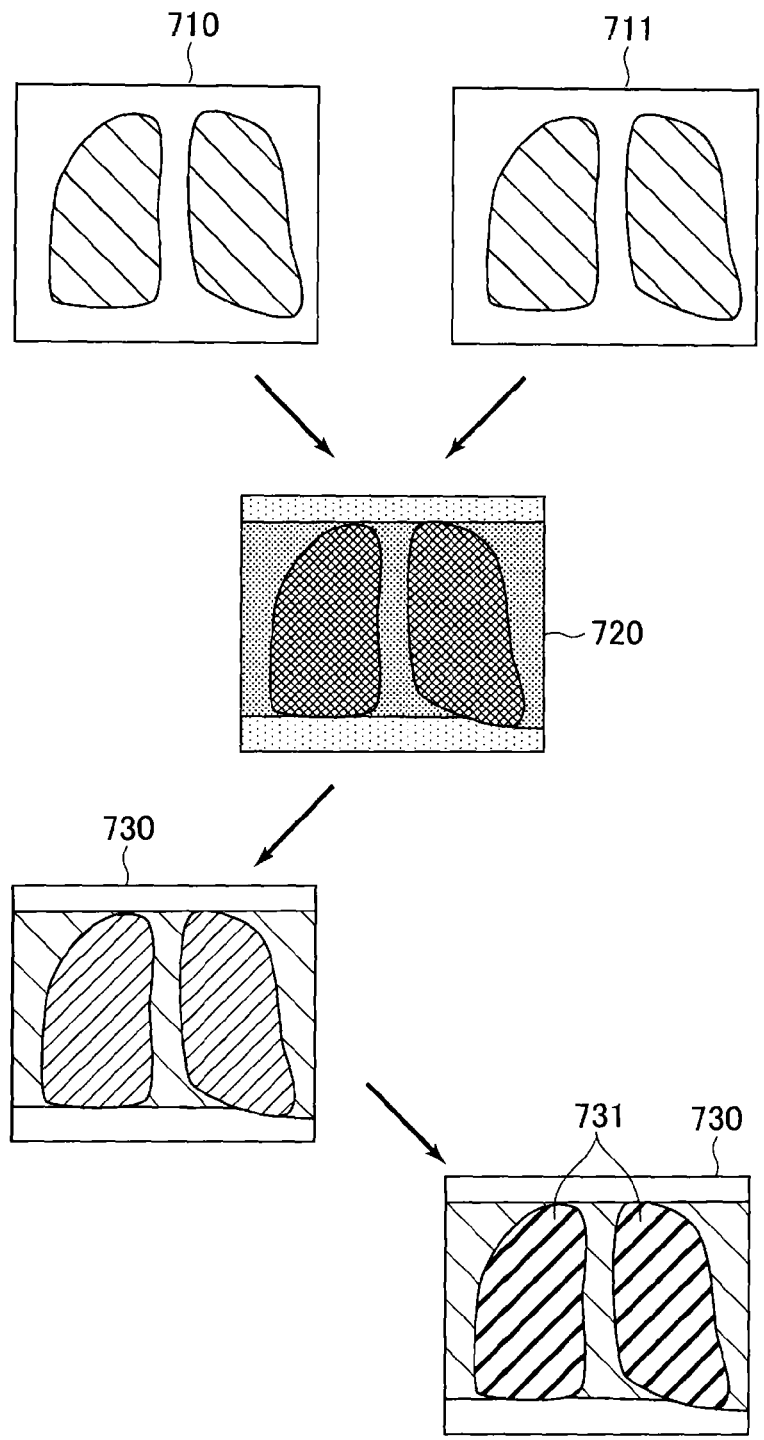
FIG. 11 is a diagram graphically showing projection data, difference projection data, and a SD map.

A specific example is described in reference to FIG. 11. FIG. 11 is a diagram graphically showing projection data, difference projection data, and a SD map. The difference calculator 31A generates difference projection data 720 by determining the difference between the projection data 710 in a specific view ($\phi1$) and the projection data 711 in a view ($\phi2$) next to the view ($\phi1$). The second statistical processor 35A generates a SD map 730 of the difference projection data 720. Then, the noise processor 36A specifies the region 731 with a standard deviation SD above a preset threshold in the SD map 730. Subsequently, the noise processor 36A performs noise-reduction processing on the projection data of the region 731. For the projection data of 1,200 views for example, the difference calculator 31A generates difference projection data for 1,200 views. Moreover, the second statistical processor 35A generates an SD map for 1,200 views. Then, the noise processor 36A performs noise-reduction processing on the projection data of the region with a standard deviation SD above the threshold among the projection data of 1,200 views.

When processing with the noise processor 36A is completed, the image processor 3A outputs the projection data of a plurality of views to the image generator 4. That is, the image processor 3A outputs the projection data of the plurality of views including the projection data treated with noise-reduction processing to the image generator 4. The image generator 4 reconfigures medical image data such as three-dimensional image data based on the projection data of the plurality of views.

As above, the X-ray CT apparatus in the second embodiment performs noise-reduction processing on the projection data in a region with a standard deviation SD in the SD map above the threshold. In this way, it is possible to reduce noise while minimizing deterioration of the data quality due to noise-reduction processing. That is, the X-ray CT apparatus in the second embodiment performs noise-reduction only on the projection data of regions in which the standard deviation SD in the SD map is above the threshold and the noise level is relatively high. In this way, it is possible to reduce noise while minimizing deterioration of the data quality.

In addition, the first statistical processor 33A or the second statistical processor 35A corresponds to an example of the "statistical processing part."

(Selection Part 38)

The selection part 38 selects projection data with the standard deviation SD of the difference projection data above a preset threshold, and sets such that reconfiguration with the image generator 4 is not performed. For example, the selection part 38 flags projection data with a standard deviation SD of the difference projection data above the threshold. The image processor 3A outputs projection data of a plurality of views to the image generator 4. The image generator 4 reconfigures medical image data such as three-dimensional image data based on the projection data of the plurality of views except the flagged projection data. Alternatively, the image processor 3A may also output to the image generator 4 the projection data of the plurality of views except the projection data with a standard deviation SD of the difference projection data above the threshold. In this case, the image generator 4 reconfigures medical image data such as three-dimensional image data based on the projection data of the plurality of views output from the image processor 3A.

Figure 12:
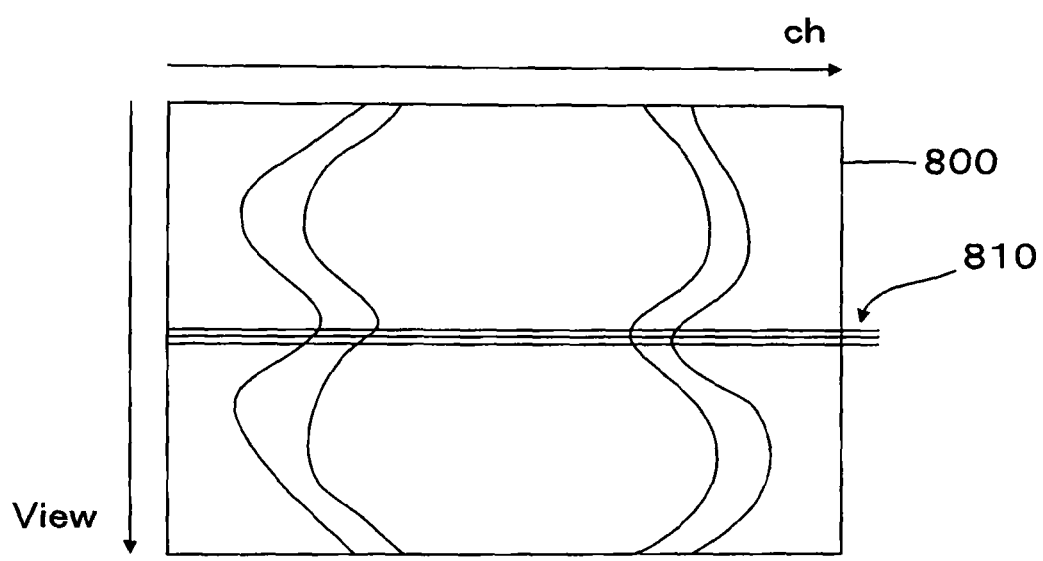
FIG. 12 is a diagram graphically showing a sinogram.

The concept of processing at the selection part 38 is described in reference to FIG. 12. FIG. 12 is a diagram graphically showing a sonogram. In FIG. 12, the vertical axis indicates the view direction and the horizontal axis indicates the channel direction. The image 800 is a sonogram obtained with the X-ray CT apparatus. Projection data 810 is data with a standard deviation SD of the difference projection data above the threshold. The image generator 4 reconfigures medical image data such as three-dimensional image data based on the projection data of a plurality of views except the projection data 810.

As above, the X-ray CT apparatus reconfigures medical image data except the projection data with a standard deviation SD of the difference projection data above the threshold and a relatively high noise level. In this way, it is possible to improve the image quality of the medical image data obtained by reconfiguration.

The function of the image processor 3A may be executed by a program. As an example, the image processor 3A is comprised of a processing unit (not shown) and a storage (not shown). As this processing unit, CPU, GPU, ASIC, etc., respectively, can be used. Moreover, as the storage, ROM, RAM, HDD, etc. can be used. In the storage, a difference calculating program, a first statistical processing program, a second statistical processing program, a noise processing program, and a selection program are stored. The first statistical processing program is used for execution of the function of the first statistical processor 33A. The second statistical processing program is used for execution of the function of the second statistical processor 35A. The noise processing program is used for execution of the function of the noise processor 36A. The selection program is used for execution of the function of the selection part 38. A processing unit such as CPU executes the function of each part by executing the program stored in the storage.

The medical image processing apparatus 1A may not comprise the second statistical processor 35A and the selection part 38 if processing is performed by the first statistical processor 33A and the noise processor 36A. Moreover, the medical image processing apparatus 1A may comprise the first statistical processor 33A and the selection part 38 if processing is performed by the second statistical processor 35A and the noise processor 36A. Moreover, the medical image processing apparatus 1A may not comprise the second statistical processor 35A and the noise processor 36A if processing is performed by the first statistical processor 33A and the selection part 38.

In addition, the medical imaging apparatus 90 may comprise the function of the medical image processing apparatus 1A.

Although embodiments of this invention have been described, the embodiments above are presented as examples and are not intended to limit the scope of the invention. These new embodiments can be practiced in other various forms, with various omissions, substitutions, and changes able to be made without deviating from the summary of the invention. These embodiments and variations thereof are included in the scope and summary of the invention and are also included in the invention described in the scope of the claims and any equivalent thereof.

EXPLANATION OF THE SYMBOLS 1, 1A Medical image processing apparatus
2 Image storage
3, 3A Image processor
4 Image generator
5 Display
6 Operation part
31, 31A Difference calculator
32 Removal part
33, 33A First statistical processor
34 Estimation part
35, 35A Second statistical processor
36, 36A Noise processor
37 Determination part
38 Selection part

What is claimed is:

1. A medical image processing apparatus comprising:
a difference calculator configured to receive a plurality of medical image data with different imaging positions and to determine a difference between the plurality of medical image data, so as to generate difference image data that represents the difference;
a removal part configured to remove a region corresponding to a structure from the difference image data;
a first statistical processor configured to determine a first standard deviation of a pixel value of each pixel of the difference image data with the region corresponding to the structure removed; and
an estimation part configured to estimate a second standard deviation of the pixel value of each pixel of the medical image data based on the first standard deviation.

2. The medical image processing apparatus according to claim 1, further comprising:
a second statistical processor configured to determine a third standard deviation of pixel values of each pixel in a predefined region of the difference image data, and to displace the predefined region across the difference image data to determine the third standard deviation at each position, so as to generate a SD map that represents a distribution of the third standard deviation, wherein;
the removal part is configured to remove a region corresponding to the structure from the SD map; and
the first statistical processor is configured to determine the first standard deviation based on the SD map with the region corresponding to the structure removed.

3. The medical image processing apparatus according to claim 2, wherein;
the first statistical processor is configured to determine a histogram that represents a frequency of the third standard deviation in the SD map with the region corresponding to the structure removed, so as to determine the first standard deviation from the histogram.

4. The medical image processing apparatus according to claim 1, wherein;
the plurality of medical image data are image data generated by an X-ray CT apparatus; and
the estimation part is configured to estimate the second standard deviation based on the first standard deviation and an estimation coefficient determined in advance based on imaging conditions of the X-ray CT apparatus and reconfiguration conditions of the medical image data.

5. The medical image processing apparatus according to claim 1, further comprising:
a determination part configured to determine whether or not to perform noise-reduction processing based on the second standard deviation; and
a noise processor configured to perform the noise-reduction processing on the medical image data when it is determined to perform the noise-reduction processing.

6. A medical image processing apparatus comprising:
a difference calculator configured to receive a plurality of projection data with different imaging angles and to determine the difference between the plurality of projection data, so as to generate difference projection data that represents the difference;
a statistical processor configured to determine a standard deviation of the difference projection data; and
a noise processor configured to perform noise-reduction processing on the difference projection data with the standard deviation above a preset threshold.

7. The medical image processing apparatus according to claim 6, wherein:
the statistical processor is configured to determine the standard deviation of the pixel values of each pixel in a predefined region of the difference projection data, and to displace the predefined region across the difference projection data to determine the standard deviation at each position, so as to generate a SD map that represents a distribution of the standard deviation; and
the noise processor is configured to specify a region with the standard deviation above a preset threshold in the SD map, and to perform the noise-reduction processing on the projection data of the specified region.

8. The medical image processing apparatus according to claim 6, further comprising:
an image generator configured to perform reconfiguration processing on the plurality of projection data in which the projection data with the standard deviation above the preset threshold has been removed, so as to generate medical image data.

9. A medical imaging apparatus comprising:
an imaging part configured to generate a plurality of medical image data with different imaging positions by imaging at a plurality of positions for a subject;
a difference calculator configured to determine a difference between the plurality of medical image data, so as to generate difference image data that represents the difference;
a removal part configured to remove a region corresponding to a structure from the difference image data;
a first statistical processor configured to determine a first standard deviation of the pixel values of each pixel of the difference image data with the region corresponding to the structure removed; and
an estimation part configured to estimate a second standard deviation of the pixel value of each pixel of the medical image data based on the first standard deviation.

10. A method of processing medical images comprising:
in response to a plurality of medical image data with different imaging positions, determining a difference between the plurality of medical image data, so as to generate difference image data that represents the difference;
removing a region corresponding to a structure from the difference image data;
performing first statistical processing of determining a first standard deviation of a pixel value of each pixel of the difference image data with the region corresponding to the structure removed; and
estimating a second standard deviation of the pixel value of each pixel of the medical image data based on the first standard deviation.

11. A medical imaging apparatus comprising:
an imaging part configured to image a subject, so as to generate a plurality of projection data with different imaging angles;
a difference calculator configured to receive a plurality of medical image data with different imaging angles and to determine a difference between the plurality of projection data, so as to generate a plurality of difference projection data;
a statistical processing part configured to determine a standard deviation of the difference projection data; and
a noise processor configured to perform noise-reduction processing on the difference projection data with the standard deviation above a preset threshold.

12. A method of processing medical images comprising:
in response to a plurality of projection data with different imaging angles, determining a difference between the plurality of projection data, so as to generate a plurality of difference projection data that represents the difference;
determining a standard deviation of the difference projection data; and
performing noise-reduction processing on the difference projection data with the standard deviation above a preset threshold.

* * * * *